United States Patent [19]

Powell

[11] 4,327,731
[45] May 4, 1982

[54] MOISTURE INDICATOR

[76] Inventor: Nelson B. Powell, 1369 Zurich Ter., Sunnyvale, Calif. 94087

[21] Appl. No.: 166,557

[22] Filed: Jul. 7, 1980

[51] Int. Cl.$^3$ ............................................. A41B 13/02
[52] U.S. Cl. ........................................ 128/287; 435/14
[58] Field of Search ............... 128/284, 287, 290, 296, 128/155–156; 252/408

[56] References Cited

U.S. PATENT DOCUMENTS

| | | | |
|---|---|---|---|
| 3,918,454 | 11/1975 | Korodi et al. | 128/287 |
| 3,952,746 | 4/1976 | Summers | 128/287 |
| 4,192,311 | 3/1980 | Felfoldi | 128/287 |
| 4,211,845 | 7/1980 | Genshaw et al. | 435/14 |
| 4,231,370 | 11/1980 | Mroz et al. | 128/287 |

*Primary Examiner*—C. Fred Rosenbaum
*Attorney, Agent, or Firm*—Owen, Wickersham & Erickson

[57] ABSTRACT

A moisture indicator employs an enzymatic reaction, a substrate and a chromogen for use in disposable diapers, sanitary napkins, surgical dressings, absorbent pads, garments, and like articles, or for use in any instance where moisture is to be detected. The moisture indicator, which is mounted, applied to, or built into the garment, diaper, pad or other article, is comprised of a chromogenic material, enzymes, such as those commonly used to test for carbohydrates in urine or other fluids, and a substrate material which will react with the selected enzyme or enzymes in the presence of moisture. The enzyme system or systems and the indicator agent or agents can be applied together to filter paper, wood strips, plastic fibrous materials, non-woven fabrics, or any absorbent materials for the purpose of subsequently verifying visually the presence of moisture.

12 Claims, 3 Drawing Figures

MOISTURE INDICATOR

BACKGROUND OF THE INVENTION

This invention relates to a system for indicating the presence of moisture in absorbent pads, such as disposable diapers, surgical dressings, sanitary napkins, etc., and to garments such as diapers and other absorbent materials incorporating the moisture indicating system. An enzymatic system used in conjunction with a chromogen visually signals the presence of moisture. The invention may further be quantitatively used to signal the presence of degrees of moisture.

In general, the prior art shows indicators which are dependent upon masking mechanisms where darker dyes are exposed when moistened, and/or non-enzymatic chemical interactions wherein color changes are dependent upon the presence or absence of acidity (e.g., litmus paper indicators), halides, which are potentially toxic, or other indicators which are complicated, uneconomical, hazardous or otherwise unsatisfactory to the wearer or user.

For example, Baker et al. U.S. Pat. No. 3,675,654 utilizes dry agents between a translucent backing and an absorbent pad, including a water soluble dye mixed with a masking agent such as talcum powder. When the pad becomes moistened, the water soluble dye becomes visible.

Likewise, Wang U.S. Pat. No. 3,759,261 adds multiple masking layers of cloth or paper over a printed pattern. When the diaper is wet, the originally opaque masking layers become translucent, revealing the printed pattern.

Similarly, Sheppard et al. U.S. Pat. No. 3,702,610 employs a water dispersible dye-containing adhesive in a spaced visible pattern to bond layers of a diaper or sanitary napkin together. When the item has been dropped in a toilet, water eventually disperses the dye-containing adhesive. When the adhesive no longer forms a discrete pattern, this informs the user of the disposable diaper or napkin that it can then be successfully flushed down the toilet. A later refinement of Sheppard was Timmons et al. U.S. Pat. No. 4,022,221, which applied the same mechanism to a different function, i.e., moisture indication to determine whether or not the diaper was in need of changing.

While all of these systems involving dyes and masking have been somewhat effective to indicate the presence of moisture, they have been unduly complicated, have required substantial quantities of materials, and as a rule have been non-discrete and non-quantitative indicators.

Other patents have disclosed systems which rely simply on chemicals which change color when wet. For example, Summers U.S. Pat. No. 3,952,746 discloses an elaborate system of transparent windows and pockets placed in a diaper, using litmus paper, food coloring, or "humidity indicator paper" to detect moisture. Summers' patent is directed more toward diaper construction than at developing a system of moisture indication.

Likewise, Eidus U.S. Pat. No. 3,731,685 proposed a moisutre indicating strip or wick as a mechanism to be attached to a garment for the purpose of detecting moisture. The patent refers to chemicals which change color when wet such as litmus paper or food coloring.

Korodi et al. U.S. Pat. No. 3,918,454 sets forth a mechanism for diaper construction involving an indicator layer impregnated with dye which becomes visible when wet. Apertures in the absorbent layer of the diaper conduct wetness to the indicator layer.

Shaw, in U.S. Pat. No. 2,681,032, uses a mechanical principle as a moisture indicator. When the diaper becomes wet, a low-wet strength element breaks, moving a colored indicator into registry with an aperture through which it is visible.

SUMMARY OF THE INVENTION

The present invention improves over the prior art by combining a unique mechanism and a practical, substantially non-toxic moisture indicator which utilizes moisture-activated enzymatic systems and chromogens or pigment-producing agents. By taking advantage of an enzyme system, the present invention increases the sensitivity and specificity of the moisture indicator with small amounts of reagent materials and permits a method of quantitative as well as qualitative moisture indication. Enzymes are protein materials which catalyze oxidation, reductions or other reactions and do not interact with the chemical substances themselves. Therefore, only minute amounts of the reagents are required, yielding discrete and obvious chemical reactions. Enzymes simplify the moisture indication system, eliminate potential substantial toxicity and minimize the possibility of staining the wearer in the case of diapers and other worn garments, since such small amounts of the reagents are used.

The invention includes an absorbent material to which is applied a moisture indicator comprised of an enzyme system, a substrate and a chromogen. The enzyme system may be any one of a number of reactive agents, but the most common examples of such enzyme systems are those embodied in enzymatic tests strips, tablets, tapes, or fluids which are used in the medical profession, articularly those designed to test for glucose in urine, for other carbohydrates, for protein, for blood or other substances found in bodily fluids. See, e.g., Blake et al. U.S. Pat. No. 3,814,668 or Bradley et al. U.S. Pat. No. 3,233,974. Examples of systems which may advantageously be used in the present invention are embodied in glucose enzymatic test strips marketed under the trademark "Tes-Tape" by Eli Lilly & Co., Indianapolis, Ind., and under the trademark "Keto-Diastix" by Ames Division of Miles Laboratories, Inc., Elkhart, Ind. Each of these systems includes two enzymes used together to test for glucose, and a chromogen. An absorbent material is impregnated with the enzymes glucose oxidase and peroxidase, along with an oxidizable chromogen substance. The "Tes-Tape" system uses orthotolidine as the oxidizable chromogen, while the other example product uses potassium iodide. When the impregnated material is dipped into a liquid (e.g. urine) containing glucose, the glucose oxidase catalyzes the reaction of glucose in the urine with oxygen from the air to form gluconic acid and hydrogen peroxide. The enzyme peroxidase then catalyzes the reaction of hydrogen peroxide and the chromogen, to produce a color. The oxidized orthotolidine of "Tes-Tape" yields a blue color, while oxidized potassium iodide forms colors ranging from green to brown, for quantitative analysis. The "Tes-Tape" product also enables semiquantitative analysis, by the addition of a yellow dye to the paper. This extends the quantitative color range of the test from yellow (no glucose present) to light green to deep blue (highest concentration of glucose).

The described systems are simply examples of an enzyme system and chromogens that can be used with the present invention. Other suitable systems may be used. In any event, the enzyme system and chromogen preferably are applied to an absorbent material impregnated with a substate material matched to the particular enzyme system used. For example, glucose, in dry form, is used as the substrate if a glucose test system such as the "Tes-Tape" system or the "Keto-Diastix" system is used. When moisture is present and reaches the substrate material, it releases some of the substrate material into the adjacent enzyme and chromogen system, and visible color is produced. Semiquantitative results can be achieved if quantitative or semiquantitative systems such as those described above are employed, since varying degrees of moisture in the substrate will release varying concentrations of dissolved glucose to the enzyme and chromogen system.

According to the invention the described system may be applied at a strategic location in a diaper, surgical dressing, sanitary napkin or other wearable absorbent pad. In a disposable diaper, having a translucent, moisture-impermeable outer layer, the testing device of the invention may be applied, in the form of a disc or strip, just beneath the translucent layer and in directed contact with one of the inner absorbent layers of the diaper. The application of the system may be directed to the absorbent diaper layer, or it may be directed to an absorbent disc or strip which is applied to the absorbent site. When the wearer is wet, there is an immediate visual indication, and this may be semiquantitative as described above.

In the case of a soft fabric, washable diaper, a wetness indicating disc or strip of the invention may include a tacky material at its underside so that it can be applied with pressure to the outside of the diaper, and later removed when the diaper is to be laundered.

Accordingly, a moisture indicating system of the invention includes a chromogen capable of producing a visible pigment upon entering into a specific chemical reaction with the chromogen when a substrate material is present in solution. The chromogen, the enzyme means and dry substrate material are supported on an absorbent carrying medium. Thus, in the presence of moisture the dry substrate material becomes dissolved, causing the enzyme means to effect the specific chemical reaction, yeildng a visible pigment from the chromogen. Varying degrees of moisture produce varying amounts of substrate in solution from the dry substrate, and thereby produce varying concentrations of the visible pigment, so that a semiquantitative analysis of wetness is possible.

It is therefore among the objects of the invention to provide, for use with diapers, other wearable absorbent devices, and other moisture indication applications, an improved moisture indicating system which is simple and effective, completely safe, stable over extended periods and under considerable heat, and which is also inexpensive to produce and simple and reliable in use. These and other objects, advantages and features of the invention will be apparent from the following description of a preferred embodiment, considered in conjunction with the accompanying drawings.

DESCRIPTION OF THE PREFERRED EMBODIMENTS

Figure 1:
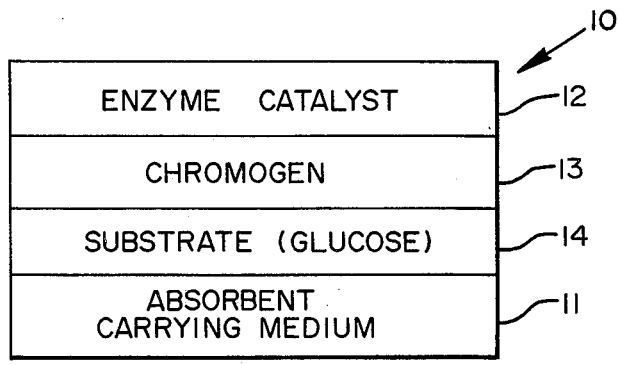
FIG. 1 is a block diagram indicating the components of a moisture indicating system according to the invention.

In the drawings, FIG. 1 indicates in block diagram form the components of moisture indicating system 10 according to the invention. The system is applied to an absorbent carrying medium 11, which may be part of a diaper or other such articles, or may be a separate disc or strip to be applied to any location where moisture detection is needed. Numerous industrial and home applications are possible. In any event, the absorbent carrying mmedium 11 supports an enzymatic test system 12 for a specified subtrate such as glucose, protein, etc., a chromogen 13, or agent which produces a pigment when it enter into a specfic chemical reaction, and the substrate 14 itself in dry form, which may be dry glucose.

For purposes of producing a moisture indicating device with the system 10, these elements may be separated so that they are impregnated indifferent layers. The layers preferably are of absorbent paper, such as filter paper, which is porous and easily impregnated with the reagents and enzymes. The enzymatic test system with the chromogen may be in one layer, so that it may comprise the equivalent of a glucose enzymatic test strip as described previously. Thus, if a glucose system is chosen, one layer may essentially comprise either of the products "Tes-Tape" or "Keto-Diastix" referred to above, or either of the systems described in Blake et al. U.S. Pat. No. 3,814,668 or Bradley U.S. Pat. No. 3,233,974. These systems, particularly the "Tes-Tape" product, are completely safe as used in a baby's diaper, and have great latitude in storage and shelf life. The manufacturers of the two trademarked products described recommend that their products be stored below 86° F., but it has been found that even after heating the "Tes-Tape" at 200° F. for a considerable period of time, it still worked as an indicator of glucose in an aqueous solution. The product is semiquantitative, in that the pigment produced by its chromogen is a blue color, and a stable, non-reactive yellow is used as a base of the strip. When aqueous glucose is present, the blue pigment is produced, and in concentration corresponding to the concentration of glucose. The range of color is from pure yellow, when no glucose in solution is present, to a nearly pure deep blue at a very high concentration of aqueous glucose. Intermediate concentrations produce various pigments of green, from yellow-green through turquoise. The other glucose enzymatic system, "Keto-Diastix," also produces at least semi-quantitative results as described previously.

Other glucose test systems may be employed, but enzymatic systems are greatly preferred over purely chemical systems, because of their safety and ability as catalysts to turn over a large volume of reagents. Only small quantities of the enzymes are therefore needed.

If the moisture indicating system of the invention is formed in layers, a second layer comprises the substrate material 14, which may be glucose, in dry, non-aqueous state. This substrate layer 14 is assembled into contact with and bonded to the other layer having the enzyme system 12 and the chromogen 13. Alternatively, all components 12, 13 and 14 of the system 10 may be deposited in a single layer of absorbent medium as indicated at 11, and this may be a disc or strip, or an absorbent layer of an item such as a diaper wherein moisture indication is desired.

In the presence of moisture, the substrate material becomes dissolved and therefore triggers the mechanism of the enzymatic test system. As varying concentrations of aqueous substrate can produce semiquantitative measurement of the substrate, as with glucose in the two example systems described above, varying degrees of moisture applied to the composite layers can produce semiquantitative results for determining degrees of wetness, by producing varying concentration of aqueous glucose.

In a system utilizing glucose as the substrate, the use of D-glucose, a monosaccharide, is preferred. It is the simplest sugar and will readily react in the enzymatic system to yield reliable results.

Since quantitative sensitivity is not required in a diaper wetness indicator, shelf-life and latitude in storage are greatly increased with the present invention, as compared to the use of a glucose enzymatic test system for quantitative glucose testing.

If the absorbent carrying medium 11 is a separate layer, forming a moisture-indicating disc or strip 10, instead of being a part of the article in which moisture is being detected, such as a diaper, the underside of the layer 11 may include an adhesive for sticking the disc or strip to a diaper or other pad, particularly a washable cloth diaper. Such an adhesive is applied to the underside of the layer 13 in such a way that the ability of the disc 10 to absorb moisture therethrough is not seriously impaired.

Figure 2:
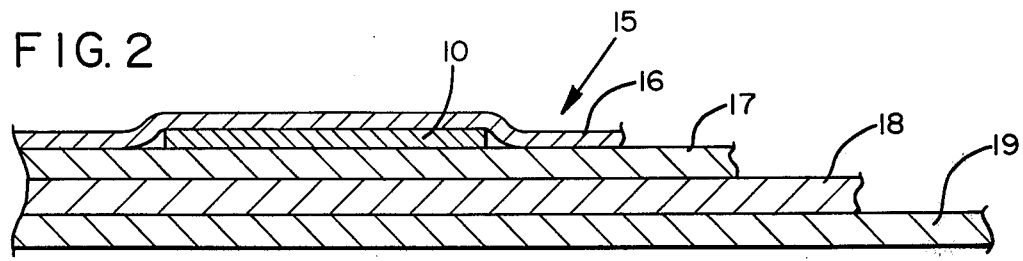
FIG. 2 is a sectional view showing a moisture indicator in disc or strip form incorporated into a disposable-type diaper.

FIG. 2 shows a moisture indicating disc or strip 10 in sectional view, as it might be incorporated in a disposable diaper 15 according to the invention. As is typical, such a diaper is of layered construction, with a translucent, moisture-impermeable outer layer 16, as of a flexible plastic material, and a series of absorbent layers 17, 18, 19, etc. These absorbent layers are usually of paper tissue or gauze-like material, and they may be successively more absorbent toward the outside, i.e., toward the impermeable layer 16, in order to draw moisture away from wearer as much as possible. The moisture indicating disc 10 is positioned between the outermost absorbent diaper layer 17 and the translucent impermeable cover material 16, so that it receives moisture from the diaper and is visible from the outside. It is thus effective to indicate wetness and, to some extent, degrees of wetness. In this embodiment of the invention, the disc or strip 10 may be retained in position in any suitable manner, as by adhesive on the side facing the absorbent diaper layers, or by adhesive engaging the inside surface of the moisture-impermeable layer 16.

Figure 3:
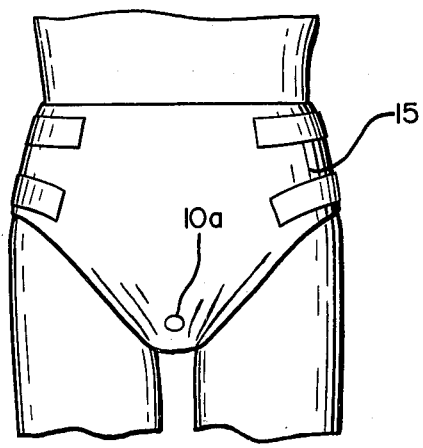
FIG. 3 is a frontal view of a diaper of the invention incoporating the moisture indicating system of the invention, the diaper being shown as worn by an infant.

FIG. 3 shows a moisture-indicating diaper 15 of the invention as worn by an infant, with a moisture indicator 10a shown located in frontal crotch area. Other positions may be suitable, but should be at or in close proximity to the crotch area, while also permitting easy visibility. The reagents of the moisture indicator 10a may be applied directly to the diaper, as outlined above, or may be in the form of a self-supporting disc or strip 10 as in FIG. 2. If the moisture indicator 10a is located low enough in the crotch area, it is effective in many cases to detect the presence of fecal wetness. A second moisture indicator may be located at the rear, if desired, for this purpose.

The moisture indicating system of the invention also may be used with surgical dressings, sanitary napkins or other wearable absorbent items where the signaling of the presence of moisture may be desired. It is therefore seen that a moisture indicating device in a diaper, surgical dressing or other absorbent pad incorporating the device under the principles of the invention provide a completely safe, simple and inexpensive system for detecting the presence of moisture and the need for a diaper. The system provides reliability, ease of detection, and semiquantitative indication. The utility and advantages of the invention are not limited to diapers or wearable pads, but extend to numerous situations wherein the detection of moisture is needed. To those skilled in the art, various changes to the specific disclosures of the preferred embodiment described above will be apparent without departing from the essence and scope of the invention. The described embodiment is illustrative of the principles of the invention but is not intended to be limiting.

I claim:

1. A disposable diaper including a moisture indicating system, said diaper including inner absorbent layers and an outer translucent moisture-impermeable layer, comprising:

a chromogen capable of producing a visible pigment upon entering into a specific chemical reaction;

enzyme means for effecting said specific chemical reaction with the chromogen when a substrate material in solution is present;

the substrate material, in dry form;

absorbent carrying medium supporting the chromogen, the enzyme means and the dry substrate material;

the absorbent carrying medium being in disc-like form and positioned just underneath the translucent, moisture-impermeable layer and against the outermost absorbent layer, with means for attaching the disc-like moisture indicating system to at least one of the adjacent layers, whereby, in the presence of moisture the dry substrate becomes dissolved, causing the enzyme means to effect the specific chemical reaction, thereby yielding a pigment from the chromogen which is visible through the outer translucent layer.

2. A disposable diaper including a moisture indicating system, said diaper including inner absorbent layers and an outer translucent moisture-impermeable layer, comprising:

a chromogen capable of producing a visible pigment upon entering into a specific chemical reaction;

enzyme means for effecting said specific chemical reaction with the chromogen when a substrate material in solution is present;

the substrate material, in dry form;

absorbent carrying medium, comprising an absorbent layer of the diaper, supporting the chromogen, the enzyme means and the dry substrate material, with the chromogen, enzyme means and substrate material applied in a discrete area directly to the abosrbent layer;

whereby, in the presence of moisture the dry substrate becomes dissolved, causing the enzyme means to effect the specific chemical reaction, thereby yielding a pigment from the chromogen which is visible through the outer translucent layer.

3. An absorbent surgical dressing including a moisture indicating system, comprising:
a chromogen capable of producing a visible pigment upon entering into a specific chemical reaction;
enzyme means for effecting said specific chemical reaction with the chromogen when a substrate material in solution is present;
the substrate material, in dry form;
absorbent carrying medium supporting the chromogen, the enzyme means and the dry substrate material; and
means for securing the moisture indicating system to the surgical dressing;
whereby, in the presence of moisture the dry substrate becomes dissolved, causing the enzyme means to effect the specific chemical reaction, thereby yielding a visible pigment from the chromogen.

4. The moisture indicating system of claim 1, 2 or 3, wherein the specific chemical reaction comprises oxidation of the chromogen, and wherein the enzyme means comprises means for effecting the oxidation of the chromogen in the presence of the substrate material in solution.

5. The moisture indicating system of claim 1, 2 or 3, wherein the substrate material is glucose.

6. The moisture indicating system of claim 1, 2 or 3, wherein the substrate material is glucose, wherein the specific chemical reaction comprises oxidation of the chromogen, and wherein the enzyme means comprises first enzyme means for producing an oxidizing agent in the presence of glucose in solution, by catalyzing the reaction of glucose with oxygen from the air, and second enzyme means for catalyzing the reaction of the oxidizing agent with the chromogen to oxidize the chromogen and produce the pigment.

7. The moisture indicating system of claim 6, wherein the first enzyme means is glucose oxidase, effective to catalyze the reaction of glucose with oxygen to form gluconic acid and hydrogen perioxide, and wherein the second enzyme means is a peroxidase, effective to catalyze the reaction of hydrogen peroxide with the chromogen.

8. The moisture indicating system of claim 7, wherein the chromogen is orthotolidine.

9. The moisture indicating system of claim 3, wherein the absorbent carrying medium comprises a first sheet of absorbent paper impregnated with the chromogen and the enzyme means, and a second sheet of absorbent paper impregnated with the dry substate material, said two sheets being bonded together in a disc-like form.

10. The moisture indicating system of claim 6, wherein the substrate material is D-glucose.

11. The moisture indicating system of claim 1 or 3, further including means indicating degrees of wetness, on a semiquantitative basis.

12. The moisture indicating system of claim 11, wherein the indicating means comprises a second, non-reactive pigment carried by the absorbent carrying medium, said second pigment being of a hue and strength which mixes with varying concentrations of said visible pigment from the chromogen to produce a range of colors ranging from said second pigment alone to a deep, nearly pure concentration of said visible pigment from the chromogen, varying degrees of moisture being effective to produce varying concentrations of dissolved substrate material, which in turn is effective to produce varying concentrations of said visible pigment from the chromogen.

* * * * *